United States Patent [19]
Bolotin et al.

[11] Patent Number: 5,616,474
[45] Date of Patent: Apr. 1, 1997

[54] *K. LACTIS* TRANSALDOLASE GENE PROMOTER AND USE THEREOF

[75] Inventors: Monique Bolotin, Gif-sur-Yvette; Sandrine Menart, Les Ulis, both of France

[73] Assignee: Rhone-Poulenc Rorer S.A., Antony, France

[21] Appl. No.: 374,686

[22] PCT Filed: Jul. 28, 1993

[86] PCT No.: PCT/FR93/00771

§ 371 Date: Feb. 1, 1995

§ 102(e) Date: Feb. 1, 1995

[87] PCT Pub. No.: WO94/03618

PCT Pub. Date: Feb. 17, 1994

[30] Foreign Application Priority Data

Jul. 30, 1992 [FR] France ................... 92 09432

[51] Int. Cl.6 ............... C12P 21/00; C07H 21/04; C12N 15/63; C12N 15/67
[52] U.S. Cl. .......... 435/69.1; 435/70.1; 536/23.1; 536/24.1; 935/22; 935/23
[58] Field of Search ................. 435/69.1, 69.2, 435/69.3, 69.4, 69.5, 69.51, 69.52, 69.6, 69.7, 69.8, 69.9, 70.1; 536/183, 23.1, 23.2, 23.4, 23.5, 24.1; 935/22.41, 33, 37, 47

[56] References Cited

U.S. PATENT DOCUMENTS

5,223,408  6/1993  Goeddel et al. ............ 435/69.3

FOREIGN PATENT DOCUMENTS

0361991  4/1990  European Pat. Off. .

OTHER PUBLICATIONS

Schaff et al. "Molecular Analysis of the Structural Gene for Yeast Transaldolase" Eur. J. Biochem 188(3): 597–604 1990.
Jacoby et al. "Transaldolase Mutants In The Yeast Kluyveromyces . . . " Mol. Microbiol. 10(4) 867–876 1993.
Chen et al. "A Gene Cloning System for *Kluyveromyces lactis* . . . " J Basic Microbiol. 28(4) 211–220 1988.
Sun et al. "Purification & Crystallization of Transaldolase Isozyme I . . . "Arch. Biochem Biophys 178: 69–78 1977.

*Primary Examiner*—Mindy Fleisher
*Assistant Examiner*—Nancy J. Degen
*Attorney, Agent, or Firm*—Julie K. Smith; Martin F. Savitzky

[57] ABSTRACT

The present invention relates to DNA sequences comprising all or part of the *K. lactis* TAL1 gene promoter or of a derivative thereof and having a transcriptional promoter activity. It also relates to the use of these sequences for expression of recombinant genes.

19 Claims, 6 Drawing Sheets

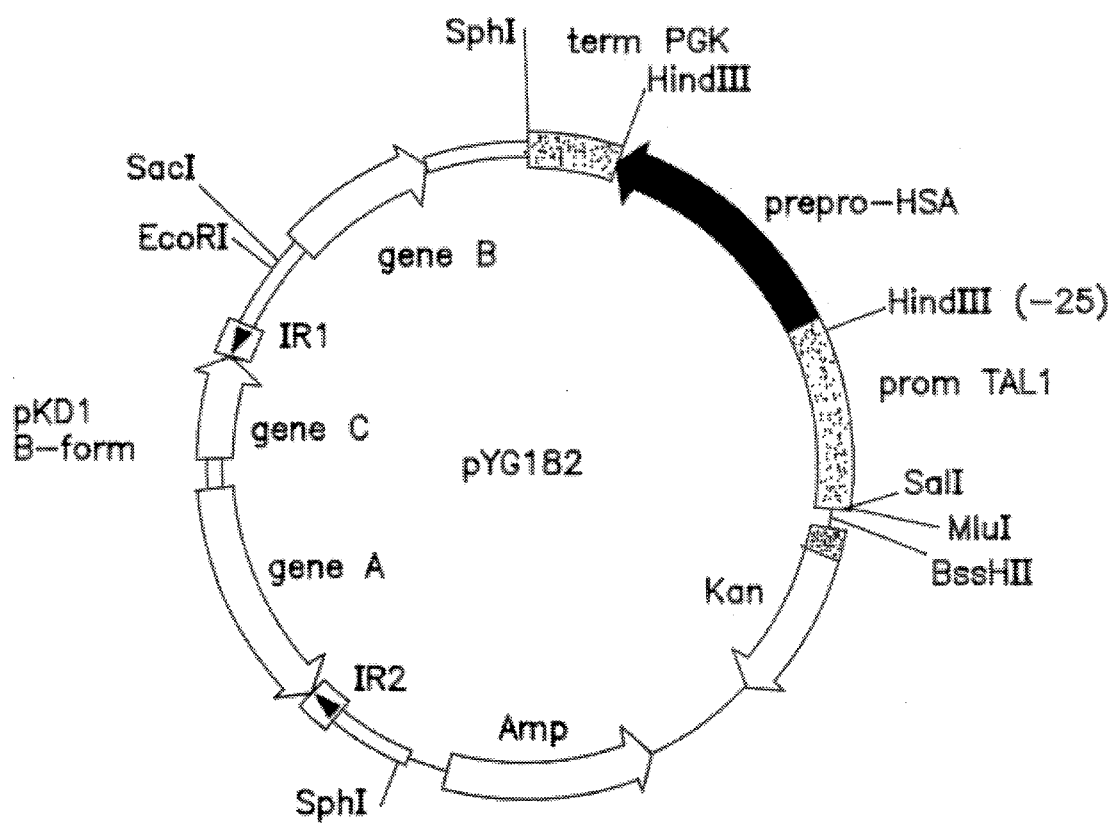
FIG. IA

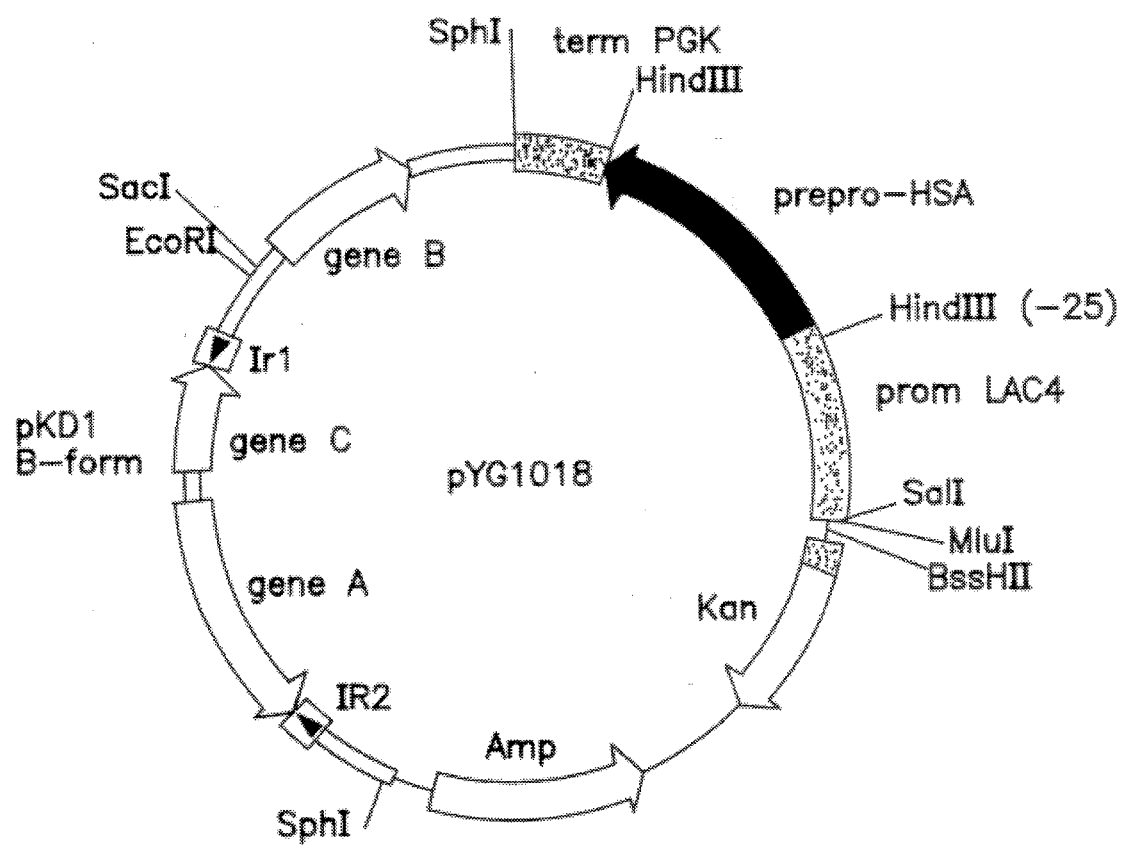
FIG. IB

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1349 base pairs
        ( B ) TYPE: nucleic acid
        ( C ) STRANDEDNESS: single
        ( D ) TOPOLOGY: linear ( i i ) MOLECULE TYPE: cDNA ( i v ) ANTI-SENSE: NO ( v i ) ORIGINAL SOURCE:
        ( A ) ORGANISM: Kluyveromyces lactis ( i x ) FEATURE:
        ( A ) NAME/KEY: CDS
        ( B ) LOCATION: 1297..1347

( x i ) SEQUENCE DESCRIPTION: SEQ ID NO:1:

```
CCCCTATCAC   ATGTAATGTA   TTAAAATCTC   TAATGTCAAA   TTTCCCAGCA   TCCAAAGGTT      60

CTCAAGGTTC   AATCCTTCAC   TTCTGCTACC   TAATCCACAG   GTGCCTTTGT   ATAACTCCAC     120

TAATTCGCTA   CATTTTTCAT   CTCTTTGATT   CGCTTTCATT   AATAAAATAT   TACTATTCGA     180

GTTGCTATAA   CTTTTAAGAT   CATATACTTG   TGTATATATG   TTAGTTTGAT   GCTTTCTGCA     240

TTTTTCTTTA   TTTCCCTATA   GTTTCTTCTG   ATATTCTAAT   CTGGCGACAG   ATACTGGGAC     300

AAACACGTAA   ATCACACACC   ATGTCACGTG   GTTAGAGAAC   AAAAGTGAAA   TATGTGTTGG     360

TGACTGAATA   AAATGATGAA   GGGTGTTTTG   CTTAAAAACG   GTGAATAAGT   TACCCGGCTG     420

ATCTGAATAG   AATCGATTTT   CTGCTTCTCA   GCTTCCTATA   ATCAAGAAAA   ACGCCATGAC     480

CGGGTAACAT   GAATTTTTGG   GTGTCGTTAT   ACAGAGCATT   GCCATCGACA   ATGAACCAGG     540

ATGCAATCTA   AGGTGAATTT   GAATAAAATA   TAGCTCCATC   TACGACCAGG   CAAGGATCAC     600

TGGAAAGTCA   TCCCGCATAA   ACTACCCGGT   TGTCCATCCG   ATAAAATGAG   TGCCATCTAT     660

AAATCACTTT   CTTTCTTACA   AACTAGTCTG   TTTTTTCCTC   CATTATGTAA   CCATTTAAAC     720
```

| | | | | | | |
|---|---|---|---|---|---|---|
| GTTAATTCCC | CTAATGCGTC | TGAATTACTC | TCTGTTCAAA | ACAAGAAACG | AAAATCCGTA | 780 |
| CTCACAAACC | AGCGATTCCC | ATACATGCAT | ACAATGATTT | CATAACAGTT | TGACTATTGC | 840 |
| TCAGCAGGCG | TGAATCAACA | CTTTGGCCCT | GTCTAACGTT | TACGTATGCT | ATGTTCTTCT | 900 |
| CTCTTAGTTG | TATTGGGTTT | TTCCGTGGCT | TTCCTCATTT | CCTACGGCCA | TTTCTCCCTT | 960 |
| TCCCAGATTT | TTTTCTTTCT | TTGTTCTTCT | TCCTGTTATA | TAATCCGGAT | TTATCACAGT | 1020 |
| ATACAACTTT | TCAAACTTTT | GATTTATTCA | GAATTGGAAT | GATGAAATAA | TATATTTGGT | 1080 |
| ATATATATAT | AAATCAAAGG | AAAAAGGTTA | ACATTGAGTT | TTACAAAGTG | TTTTCTTCTT | 1140 |
| TTGCCAATTC | AGCTAAATTC | TTAATCGGAT | CTAATTTTTG | TTAGTAAGA | TTCTTTATTT | 1200 |
| TGAGAAGGTT | ATTGTCTATT | CTAATCTTGG | TTATTTCATT | CACCAGGAAA | CAGTAATTAC | 1260 |
| ACTCAAGTAA | TTTACCTTAT | AAATCCTACT | CAAGC ATG | TCT GAA CCA AGT GCT | | 1314 |
| | | | | Met Ser Glu Pro Ser Ala | | |
| | | | | 1 5 | | |

```
AAG AAA CAA AAG TTT GCC AAC TCT TTG GAA GCC TT                              1349
Lys Lys Gln Lys Phe Ala Asn Ser Leu Glu Ala
            10                  15
```

( 2 ) INFORMATION FOR SEQ ID NO:2:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ser Glu Pro Ser Ala Lys Lys Gln Lys Phe Ala Asn Ser Leu Glu
 1               5                   10                  15
Ala
```

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:3:

| | | |
|---|---|---|
| CTGTTTCATT | TGAAGCGCG | 19 |

( 2 ) INFORMATION FOR SEQ ID NO:4:

( i ) SEQUENCE CHARACTERISTICS:
        ( A ) LENGTH: 1226 base pairs
        ( B ) TYPE: nucleic acid
        ( C ) STRANDEDNESS: single
        ( D ) TOPOLOGY: linear ( i i ) MOLECULE TYPE: cDNA ( i v ) ANTI-SENSE: NO ( x i ) SEQUENCE DESCRIPTION: SEQ ID NO:4:

| | | | | | | |
|---|---|---|---|---|---|---|
| ACGCGTGTCG | ACGCTACCTA | ATCCACAGGT | GCCTTTGTAT | AACTCCACTA | ATTCGCTACA | 60 |
| TTTTTCATCT | CTTTGATTCG | CTTTCATTAA | TAAAATATTA | CTATTCGAGT | TGCTATAACT | 120 |

-continued

| | | | | | | |
|---|---|---|---|---|---|---|
| TTTAAGATCA | TATACTTGTG | TATATATGTT | AGTTTGATGC | TTTCTGCATT | TTTCTTTATT | 180 |
| TCCCTATAGT | TTCTTCTGAT | ATTCTAATCT | GGCGACAGAT | ACTGGGACAA | ACACGTAAAT | 240 |
| CACACACCAT | GTCACGTGGT | TAGAGAACAA | AAGTGAAATA | TGTGTTGGTG | ACTGAATAAA | 300 |
| ATGATGAAGG | GTGTTTTGCT | TAAAAACGGT | GAATAAGTTA | CCCGGCTGAT | CTGAATAGAA | 360 |
| TCGATTTTCT | GCTTCTCAGC | TTCCTATAAT | CAAGAAAAAC | GCCATGACCG | GGTAACATGA | 420 |
| ATTTTTGGGT | GTCGTTATAC | AGAGCATTGC | CATCGACAAT | GAACCAGGAT | GCAATCTAAG | 480 |
| GTGAATTTGA | ATAAAATATA | GCTCCATCTA | CGACCAGGCA | AGGATCACTG | GAAAGTCATC | 540 |
| CCGCATAAAC | TACCCGGTTG | TCCATCCGAT | AAAATGAGTG | CCATCTATAA | ATCACTTTCT | 600 |
| TTCTTACAAA | CTAGTCTGTT | TTTTCCTCCA | TTATGTAACC | ATTTAAACGT | TAATTCCCCT | 660 |
| AATGCGTCTG | AATTACTCTC | TGTTCAAAAC | AAGAAACGAA | AATCCGTACT | CACAAACCAG | 720 |
| CGATTCCCAT | ACATGCATAC | AATGATTTCA | TAACAGTTTG | ACTATTGCTC | AGCAGGCGTG | 780 |
| AATCAACACT | TTGGCCCTGT | CTAACGTTTA | CGTATGCTAT | GTTCTTCTCT | CTTAGTTGTA | 840 |
| TTGGGTTTTT | CCGTGGCTTT | CCTCATTTCC | TACGGCCATT | TCTCCCTTTC | CCAGATTTTT | 900 |
| TTCTTTCTTT | GTTCTTCTTC | CTGTTATATA | ATCCGGATTT | ATCACAGTAT | ACAACTTTTC | 960 |
| AAACTTTTGA | TTTATTCAGA | ATTGGAATGA | TGAAATAATA | TATTTGGTAT | ATATATATAA | 1020 |
| ATCAAAGGAA | AAAGGTTAAC | ATTGAGTTTT | ACAAAGTGTT | TTCTTCTTTT | GCCAATTCAG | 1080 |
| CTAAATTCTT | AATCGGATCT | AATTTTTGTT | TAGTAAGATT | CTTTATTTTG | AGAAGGTTAT | 1140 |
| TGTCTATTCT | AATCTTGGTT | ATTTCATTCA | CCAGGAAACA | GTAATTACAC | TCAAGTAATT | 1200 |
| TACCTTATAA | ATCCTACTAC | AAGCTT | | | | 1226 |

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:5:

AGCGGCCGCT         10

K. LACTIS TRANSALDOLASE GENE PROMOTER AND USE THEREOF

The present invention relates to the field of molecular biology. More particularly, it relates to a new DNA sequence having a transcriptional promoter activity, expression vectors containing this sequence, and its use for the production of recombinant proteins, for example heterologous proteins. The invention also relates to recombinant cells containing this DNA sequence.

The progress achieved in the field of molecular biology has enabled microorganisms to be modified to cause them to produce heterologous proteins. In particular, several genetic studies have been carried out on the E. coli bacterium. However, industrial use of these new production methods is still limited, in particular by problems of the effectiveness of gene expression in these recombinant microorganisms. In addition, in order to increase the performance of these production systems, investigations have been carried out to isolate strong promoters to enable high levels of expression of heterologous proteins to be obtained. With respect to E. coli, tryptophan and lactose operon promoters may be mentioned in particular.

More recently, studies on the yeast S. cerevisiae have related to promoters derived from genes involved in the glycolysis. The works on the promoter of the 3-phosphoglycerate kinase gene PGK (Dobson et al., Nucleic Acid Res. 10, 1982, 2625; Hitzeman et al., Nucleic Acid Research 1982, 7791), on that of the glyceraldehyde 3-phosphate dehydrogenase gene GAPDH (Holland et al., J. Biol. Chem. 254, 1979, 9839; Musti et al., Gene 25, 1983, 133), on that of the alcohol dehydrogenase 1 gene ADH1 (Bennentzen et al., J. Biol. Chem. 257, 1982, 3018; Denis et al., J. Biol. Chem. 25, 1983, 1165), on that of the enolase 1 gene ENO1 (Uemura et al., Gene 45, 1986, 65), on that of the GAL1/GAL10 gene (Johnston and Davis, Mol. Cell. Biol. 4, 1984, 1440) or on that of the CYC1 gene (Guarente and Ptashne, PNAS 78 (1981) 2199) may be mentioned in particular.

Genetic tools have recently been developed in order to make use of the yeast Kluyveromyces as the host cell for production of recombinant proteins. The discovery of a plasmid of the 2-micron type originating from K. drosophilarum (plasmid pKD1- EP 241 435) has enabled a very efficient host/vector system to be established for production of recombinant proteins (EP 361 991). However, the promoters used in this system have not been optimized to date. In particular, they are essentially heterologous promoters, that is to say originating from other microorganisms, such as, in particular, S. cerevisiae. This situation may result in various disadvantages, and in particular limit the activity of the promoter due to the absence of certain elements of the transcriptional machinery (for example trans-activators), cause a certain toxicity to the host cell because of an absence of regulation, or affect the stability of the vector.

Under these conditions, the lack of strong homologous promoters in the case of Kluyveromyces constitutes a limiting factor in the industrial use of this expression system.

The Applicant has now identified, cloned and sequenced a genome region of Kluyveromyces lactis having a transcriptional promoter activity (SEQ ID No. 1). More precisely, this region corresponds to a gene promoter coding for a transaldolase of K. lactis (called KlTAL1 gene). This region or derivatives or fragments thereof can be used in a very effective manner for production of recombinant proteins in yeasts of the genus Kluyveromyces. It is understood that this sequence may also be used in other host organisms.

Furthermore, one advantage of the promoter region obtained rests in the absence of repression by glucose, enabling use in the conventional and industrial culture media.

The present invention thus relates to a DNA sequence comprising all or part of the sequence SEQ ID No. 1 (nucleotide sequence of the fragment of 1.3 kb corresponding to the promoter KlTAL1 of K. lactis) or of its complementary strand, or of a derivative thereof, and having a transcriptional promoter activity.

In the context of the present invention, derivative is understood as meaning any sequence obtained from the sequence SEQ ID No. 1 by modification(s) of a genetic and/or chemical nature preserving a promoter activity. Modification of a genetic and/or chemical nature is understood as meaning any mutation, deletion, substitution, addition and/or modification of one or more nucleotides. Such modifications may be effected with various aims, in particular in order to prepare portable promoters, or in order to prepare promoters suitable for expression in a particular vector or host type, or in order to reduce the size, increase the activity of the transcription promoter, to generate promoters which can be induced, to improve the level of regulation or else to change the nature of the regulation. Such modifications may be carried out, for example, by in vitro mutagenesis, by introduction of additional elements of control or of synthetic sequences, or by deletions or substitutions of original elements of control.

If a derivative as defined above is realized, its transcriptional promoter activity may be demonstrated in various ways, and in particular by placing a reporter gene, the expression of which is detectable, under the control of the sequence studied. Any other technique known to the expert may of course be used to this effect.

The sequences SEQ ID Nos. 1 and 2 were obtained from a fusion bank between fragments of the K. lactis genome 2359/152 and the gene lacZ of E. coli in accordance with the protocol described in the Examples. It is understood that the expert can isolate this region by hybridization by means of a probe comprising all or part of the sequence given in FIG. 1 or its complementary strand. The derivatives according to the invention can then be prepared from this sequence, as indicated in the Examples.

The invention also relates to a recombinant DNA comprising a DNA sequence as defined above.

This recombinant DNA may contain, for example, the promoter sequence SEQ ID No. 1 or a derivative thereof, in which a restriction site is inserted, allowing this sequence to be used as a "portable" promoter (cf. SEQ ID No. 4).

This recombinant DNA preferably also contains one or more structural genes. In particular, these may be genes coding for proteins of pharmaceutical or agro-nutritional interest. By way of example, there may be mentioned enzymes (such as, in particular, dismutase superoxide, catalase, amylases, lipases, amidases, chymosin and the like), blood derivatives (such as serum albumin, alpha- or beta-globin, factor VIII, factor IX, von Willebrand factor, fibronectin, 1-alpha-antitrypsin and the like), insulin and its variants, lymphokines (such as interleukins, interferons, colony stimulation factors [granulocyte colony stimulating factor (G-CSF), granulocyte-macrophage colony stimulating factor (GM-CSF), macrophage stimulating factor (M-CSF)], tumor necrosis factor (TNF), T-cell replacing factor (TRF) and the like), growth factors (such as growth hormone, erythroprotein, fibroblast growth factor (FGF), epidermal growth factor (EGF), platelet derived growth factor (PDGF), transforming growth factor (TGF) and the like), apolipoproteins, antigenic polypeptides for realization of vaccines (hepatitis, cytomegalovirus, Epstein-Barr, herpes and the like), or else fusions of polypeptides, such as, in particular, fusions comprising an active part fused to a stabilizing part (for example fusions between albumin or albumin fragments and the virus receptor or a part of a virus receptor [CD4 and the like]).

Even more preferably, the recombinant DNA also contains signals which allow secretion of the expression product of the said structural gene or genes. These signals may correspond to natural secretion signals of the protein in question, but they may be of a different origin. In particular, secretion signals derived from yeast genes may be used, such as those of the genes of killer toxin (Stark and Boyd, EMBO J. 5 (1986) 1995) or of alpha-pheromone (Kurjan and Herskowitz, Cell 30 (1982) 933; Brake et al., Yeast 4 (1988) S436).

In a particular embodiment of the invention, the recombinant DNA is part of an expression plasmid, which may be of autonomous or integrated replication.

In particular, the vectors of autonomous replication can be obtained by using autonomous replication sequences in the host chosen. In the case of yeast in particular, these may be replication sources derived from plasmids (pKD1, 2µ and the like) or chromosome sequences (ARS).

The integrated vectors may be obtained, in particular, using sequences homologous to certain regions of the host genome, allowing integration of the vector by homologous recombination.

The invention also relates to recombinant cells containing a DNA sequence as defined above.

The cells are advantageously chosen from yeasts, and even more preferably from yeasts of the genus Kluyveromyces. However, it is understood that the invention covers all the recombinant cells in which the promoter regions according to the invention are active, whether eukaryotic or prokaryotic cells are concerned.

Eukaryotic cells which may be mentioned are thus vegetable or animal cells, yeasts or fungi. In particular, with reference to yeasts, there may be mentioned yeasts of the genus Saccharomyces, Pichia, Schwanniomyces or Hansenula. With reference to animal cells, there may be mentioned the cells COS, CHO, C127 and the like. Among the fungi which may be used in the present invention, there may be mentioned more particularly Aspergillus ssp. or Trichoderma ssp. Prokaryotic hosts which may be used are bacteria such as *Escherichia coli*, or those belonging to the genera Corynebacterium, Bacillus or Streptomyces.

The activity of the transcription promoter of sequences according to the invention in these various hosts may be verified, for example, by introducing into the host cell in question a recombinant DNA comprising, under the control of the promoter sequence studied, a reporter gene, the expression of which can be demonstrated in the host in question.

The recombinant cells according to the invention may be obtained by any method which enables a foreign DNA to be introduced into a cell. This may be, in particular, transformation, electroporation, conjugation, protoplast fusion or any other technique known to the expert. In respect of transformation, various protocols have been described in the prior art. In particular, this may be realized by treating whole cells in the presence of lithium acetate and polyethylene glycol in accordance with the technique described by Ito et al. (J. Bacteriol. 153 (1983), 163–168), or in the presence of ethylene glycol and dimethylsulphoxide in accordance with the technique of Durrens et al. (Curr. Genet. 18 (1990) 7). An alternative protocol has also been described in the Patent application EP 361 991. In respect of electroporation, this may be carried out in accordance with the method of Becker and Guarentte (in: Methods in Enzymology Vol 194 (1991) 182).

The invention also relates to the use of a sequence as defined above for the expression of recombinant genes. The DNA sequences according to the invention may in fact enable recombinant proteins to be produced at high levels.

The sequences according to the invention can advantageously be used for expression of genes coding for proteins of pharmaceutical or agro-nutritional interest. The proteins listed above may be mentioned by way of example.

The present invention also enables a process for the production of recombinant proteins to be realized, according to which a recombinant cell as defined above is cultured and the protein produced is recovered. The proteins listed above may be mentioned by way of example.

The process according to the invention can preferably be applied to the production of human serum albumin or one of its molecular variants. A molecular variant of albumin is understood as meaning natural variants resulting from polymorphism of albumin, mutilated forms or any hybrid protein based on albumin.

Other advantages of the present invention will become obvious by reading the examples which follow, which are to be regarded as illustrative and non-limiting.

BRIEF DESCRIPTION OF DRAWING

FIGS. 1A and 1B Restriction map of the plasmids pYG1018 and pYG182.

GENERAL CLONING TECHNIQUES

Figure 2A:
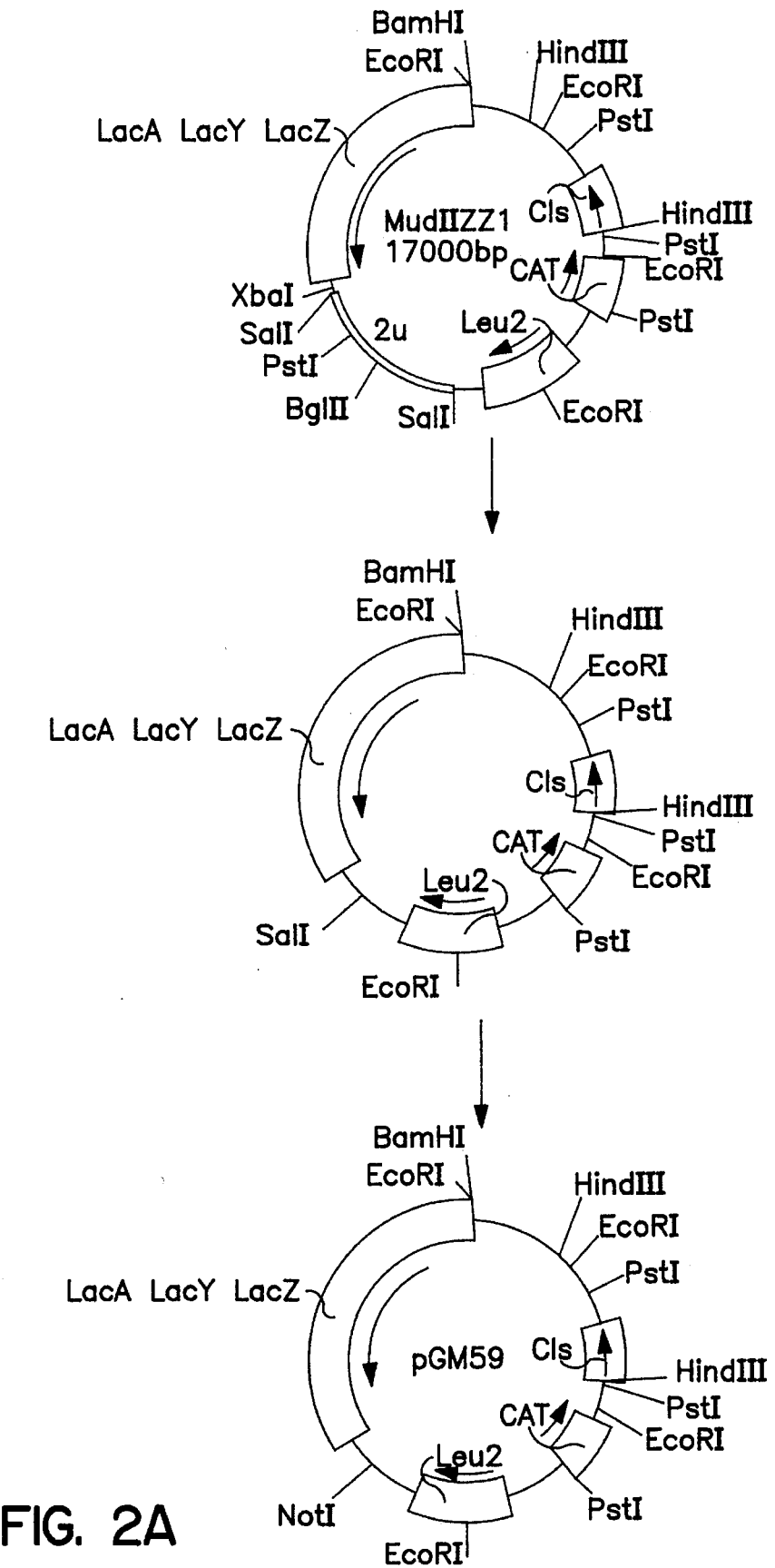
FIGS. 2A and 2B Preparation of the transposon mini-mu MudIIZK1.

The conventional methods used in molecular biology, such as preparative extractions of plasmid DNA, centrifugation of plasmid DNA in a gradient of caesium chloride, electrophoresis on agarose gel or acrylamide gel, purification of DNA fragments by electroelution, extraction of proteins with phenol or with phenol/chloroform, DNA precipitation in a saline medium using ethanol or isopropanol, transformation in *Escherichia coli* and the like, are well known to the expert and are described abundantly in the literature [Maniatis T. et al., "Molecular Cloning, a Laboratory Manual", Cold Spring Harbor Laboratory, Cold Spring Harbor, N.Y., 1982; Ausubel F. M. et al. (editors), "Current Protocols in Molecular Biology", John Wiley & Sons, New York, 1987].

The restriction enzymes were supplied by New England Biolabs (Biolabs) or Pharmacia and are used in accordance with the suppliers' recommendations.

The plasmids of the type pBR322 and pUC are of commercial origin (Bethesda Research Laboratories).

For the ligations, the DNA fragments are separated according to size by electrophoresis in agarose gel or acrylamide gel, extracted with phenol or with a phenol/chloroform mixture, precipitated with ethanol and then incubated in the presence of the DNA ligase of the phage T4 (Boehringer) in accordance with the supplier's recommendations.

Filling-in of the proeminent 5' ends is effected by Klenow fragment of DNA polymerase I of *E. coli* (Boehringer) in accordance with the supplier's specifications. Destruction of the proeminent 3' ends is effected in the presence of DNA polymerase of the phage T4 (Biolabs) used in accordance with the manufacturer's recommendations. Destruction of the proeminent 5' ends is effected by a treatment administered by the nuclease S1.

Mutagenesis controlled in vitro by synthetic oligodeoxynucleotides is effected in accordance with the method developed by Taylor et al. [Nucleic Acids Res. 13 (1985) 8749–8764].

Enzymatic amplification of DNA fragments by the so-called PCR technique [Polymerase-catalysed Chain Reaction, Saiki R. K. et al., Science 230 (1985) 1350–1354; Mullis K. B. and Faloona F. A., Meth. Enzym. 155 (1987) 335–350] is effected using a "DNA thermal cycler" (Perkin Elmer Cetus) in accordance with the manufacturer's specifications.

Verification of the nucleotide sequences is effected by the method developed by Sanger et al. [Proc. Natl. Acad. Sci. USA, 74 (1977) 5463–5467].

The transformations of *K. lactis* are effected by any technique known to the expert, an example of which is given in the text.

Unless indicated otherwise, the bacterial strains used are *E. coli* DH1 (Hanahan D., J. Mol. Biol. 166 (1983) 557) or *E. coli* JM109::(Mucts) (Daignan-Fornier and Bolotin-Fukuhara, Gene 62 (1988) 45).

The yeast strains used belong to budding yeasts, and more particularly to yeasts of the genus Kluyveromyces. The strains *K. lactis* 2359/152 and *K. lactis* SD6 were used in particular.

The strains of yeasts transformed by the plasmids are cultured in conical flasks or pilot fermenters of 2 l (SETRIC, France) at 28° C. in rich medium (YPD: 1% yeast extract, 2% bactopeptone, 2% glucose; or YPL: 1% yeast extract, 2% bactopeptone, 2% lactose) with constant agitation.

EXAMPLES

I. Isolation of the Promoter KlTAL1 of *K. lactis*.

The sequence SEQ ID No. 1 was isolated from a fusion bank between fragments of the *K. lactis* genome 2359/152 and the lacZ gene of *E. coli*. This example describes in (A) the preparation of the fusion bank and in (B) the selection and characterization of a clone of this bank carrying the promoter of the gene of the transaldolase TAL1 of *K. lactis*.

A/Preparation of the Fusion Bank

Figure 2B:
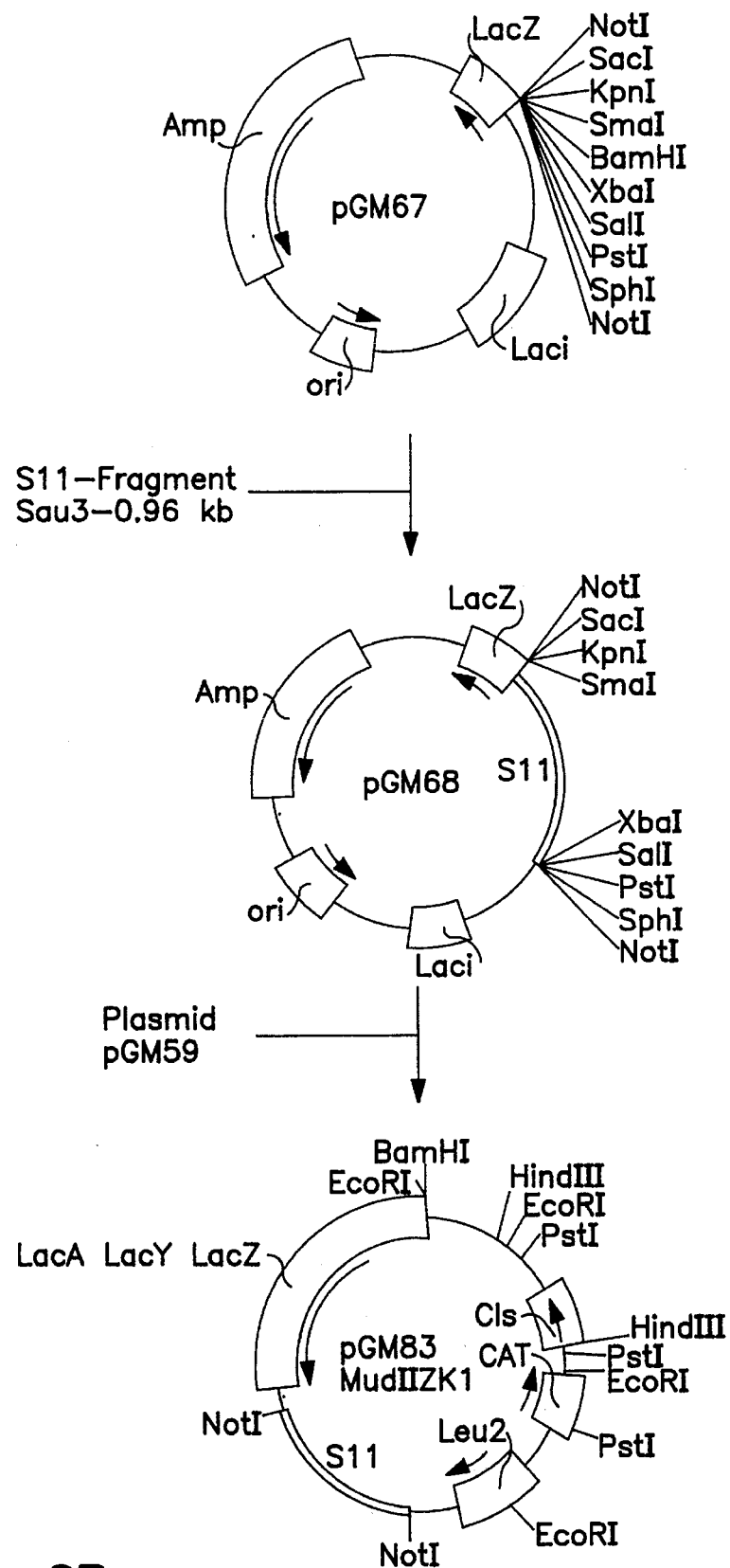
Figure 3:
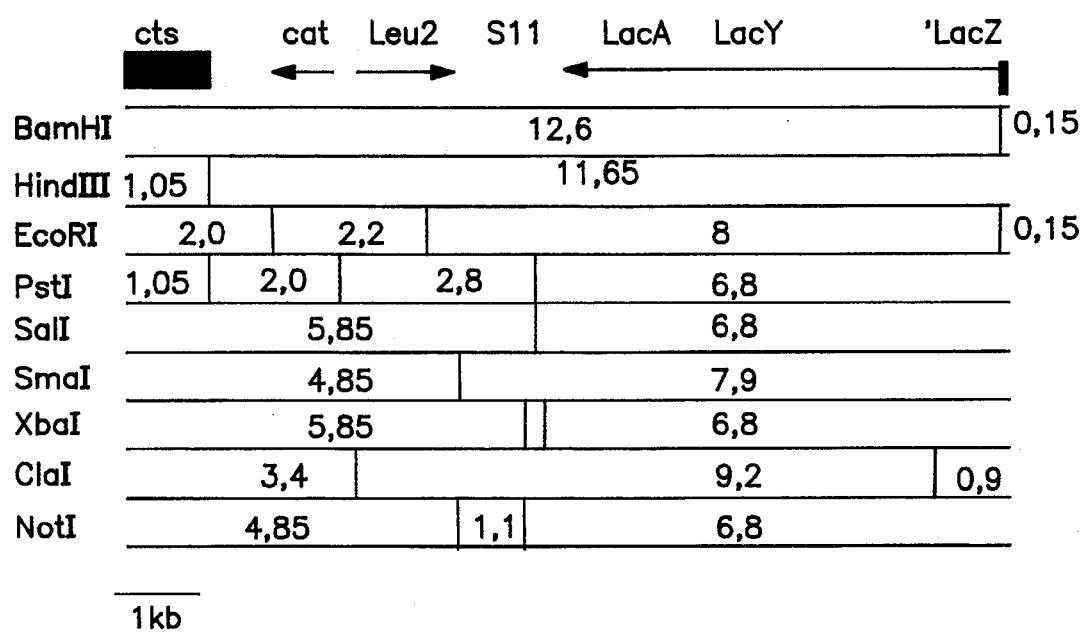
FIG. 3 Restriction map of the transposon mini-mu MudI-IZK1.

A.1. Preparation of the mini-mu Transposon MudIIZK1 (FIGS. 2 and 3).

Mini-mu MudIIZK1 was constructed from mini-mu MudIIZZ1 decribed by Daignan-Fornier and Bolotin-Fukuhara (Gene 62 (1988) 45). It was obtained by substituting the replication origin of the mini-transposon MudIIZZ1 by a functional replication origin in Kluyveromyces: the replication origin of the plasmid pKD1 (EP231 435).

A.1.1 Construction of a Cassette Carrying the Replication Origin of the Plasmid pKD1 (fragment S11).

In order to facilitate subsequent manipulations, the fragment S11 (carrying the replication origin of the plasmid pKD1) was put into the form of a NotI cassette. For this, a derivative of the plasmid pUC18 was constructed, in which the external sites of the cloning multisite (HindIII and EcoRI sites) were changed into NotI sites. This was done by digestion with the corresponding enzyme, action of the Klenow enzyme and ligation with a synthetic oligonucleotide corresponding to an NotI site [oligo d(AGCGGC-CGCT)SEQ ID No: 5; Biolabs]. The plasmid obtained is designated pGM67. The fragment S11 of 960 pb obtained by digestion with the enzyme Sau3A of the plasmid KEp6 (Chen et al., Nucl. Acids Res. 114 (1986) 4471) was then inserted at the compatible BamHI site of the plasmid pGM67. The plasmid thus obtained, designated pGM68, contains the fragment S11 in the form of an NotI cassette.

A.1.2. Suppression of the Replication Origin 2 μ of the Transposon MudIIZZ1.

The plasmid pGM15 carrying mini-mu MudIIZZ1 (Daignan-Fornier and Bolotin-Fukuhara loc. cit.) was deleted from the 2 μ regions by digestion by means of the enzyme SalI. The single SalI site thus obtained was then transformed into the NotI site by ligation of a synthetic oligonucleotide corresponding to an NotI site after action of Klenow's enzyme. The resulting plasmid is called pGM59.

A.1.3. Insertion of the Fragment S11

The cassette NotI carrying the replication origin of the plasmid pKD1 (fragment S11), originating from the modified plasmid pUC18, was then introduced into the single NotI site of the plasmid pGM59.

The plasmid obtained, designated pGM83, carries a mini-mu called MudIIZK1, which is suitable for the yeast *Kluyveromyces lactis*, as well as a functional copy of the gene LEU2 of *S. cerevisiae* capable of complementing an leu2 mutation in *K. lactis* (Kämper et al., Curr. Genet. 19 (1991) 109).The restriction map of the mini-mu MudIIZK1 is represented in FIG. 3.

A.2. Introduction of the mini-mu MudIIZK1 into the *E. coli* strain carrying the mu helper JM109::(Mucts): the strain JM109::(Mucts)::(MudIIZK1) is obtained.

The strain JM109::(Mucts) was transformed by the plasmid pGM83 containing the mini-mu MudIIZK1 in the presence of calcium chloride. After transformation, transposition was induced by thermal shock in accordance with the technique described by Castilho et al. (J. Bacteriol. 158 (1984) 488). The phage lysate obtained after induction is then used for secondary infection of the strain JM109::(Mucts). Since the strain JM109::(Mucts) is recA, the linear DNA encapsidated by the phage cannot close again to give a replicating plasmid. The integrated units [strain JM109::(Mucts)::(MudIIZK1)] are thus selected as clones resistant to chloramphenicol ($Cm^R$) and sensitive to ampicillin ($Amp^S$).

A.3. Preparation of the Genome Bank of *K. lactis* in *E. coli* DH1

DNA of high molecular weight was prepared from the strain *K. lactis* 2359/152 and partly digested by the enzyme Sau3A. The fragments having a size of 4 to 8 kb were recovered on LMP agarose gel ("Low Melting Point", SEAKEM) and cloned in the plasmid pBR322 linearized by BamHI and dephosphorylated by the action of intestinal calf phosphatase (Biolabs). 35 pools of 1000 colonies in *E. coli* DH1 were thus realized. The 1000 colonies of each pool are ampicillin-resistant and tetracycline-sensitive, which demonstrates that they have all inserted a genome DNA fragment of *K. lactis* in pBR322.

A.4. Preparation of the Fusion Bank

A.4.1. Introduction of the Genome Bank of *K. lactis* into the strain JM109::(Mucts)::(MudIIZK1).

The plasmid DNA of each pool realized in DH1 is extracted (Maniatis). This DNA is then used to transform the strain JM109::(Mucts)::(MudIIZK1) in the presence of calcium chloride. To be representative of the 1000 colonies contained in each pool of the genome bank, more than 3000 clones per pool were recovered in the strain JM109::(Mucts)::(MudIIZK1), allowing transduction.

A.4.2. Transposition of the mini-mu MudIIZK1

The fusion bank is realized by extensive transposition of the mini-mu MudIIZK1 on the plasmids forming the genome DNA bank of *K. lactis*. The mini-muductions were carried out in accordance with the protocol described by Castilho et al. (J. Bacteriol. 158 (1984) 488) and the transduced elements were selected on LBAC selective medium (LB medium (Gibco BRL) supplemented with 50 mg/l of ampicillin and 30 mg/l of chloramphenicol), the marker $Amp^R$ being contributed by the plasmid and the marker $Cm^R$ by the mini-mu. For each pool, the transpositions are performed in series, and between 10,000 and 20,000 transduced elements are recovered per pool. The DNA of the transduced elements is then extracted from a preparation of 100 ml, purified by precipitation with polyethylene glycol (Maniatis et al., 1989) and resuspended in 100 µl of water. This DNA was then used to transform *K. lactis* and select clones carrying promoters.

B/Isolation of the *K. lactis* KlTAL1 Promoter

The fusion DNA prepared above was used to transform, by electroporation, a recipient strain of *K. lactis*. This recipient strain, called SD6, carries the mutations leu2 (corresponding to the selection marker of the mini-mu MudIIZK1) and lac4–8. This latter mutation prevents the strain from growing on a medium containing lactose as the sole source of carbon, but it may be complemented by super-expression of the gene lacZ of *E. coli* coding for β-galactosidase (Chen et al., J. Basic Microbiol. 28 (1988) 211). Because of this, the expression of a protein fused to β-galactosidase should allow growth of the strain SD6 on lactose after transformation. This positive screening was used for rapid selection of clones carrying strong promoters.

B.1. Construction of the Recipient Strain *K. lactis* SD6.

The strain SD6 (Chen et al., Mol. Gen. Genet. 233 (1992) 97) was obtained by crossing the strain *K. lactis* CXJ1-7A (a, lac4–8, ura3A, ade1—1, K1, K2, pKD1) (Chen and Fukuhara, Gene 69 (1988) 181) with the strain AWJ-137 (leu2, trp1, homothallic) (Kämper et al., Curr. Genet. 19 (1991) 109), and selection of spores having the genotype $ADE^+$, uraA, leu2 and lac4–8. As the spores obtained were not capable of regeneration after transformation by protoplasts, a return crossing was undertaken with the strain CXJ1-7A. After sporulation in bulk, the spores of the genotype chosen were tested by transformation in lithium chloride with the plasmid KEp6 in accordance with a technique derived from that described by Ito et al. (J. Bacteriol. 153 (1983) 163) (the concentration of LiCl is 20 mM, i.e. 10 times less than that used by Ito for *S. cerevisiae*). The strain CXJ1-7A served as a transformation control.

The strain SD6 selected under these criteria is transformed correctly: 1 to $3 \times 10^4$ transformants per µg of DNA; and the transformants have a satisfactory stability: 30 to 40% of colonies retain the phenotype [$Ura^+$] after 6 generations in a non-selective medium.

B.2. Isolation of the KlTAL1 Promoter.

Figure 4:
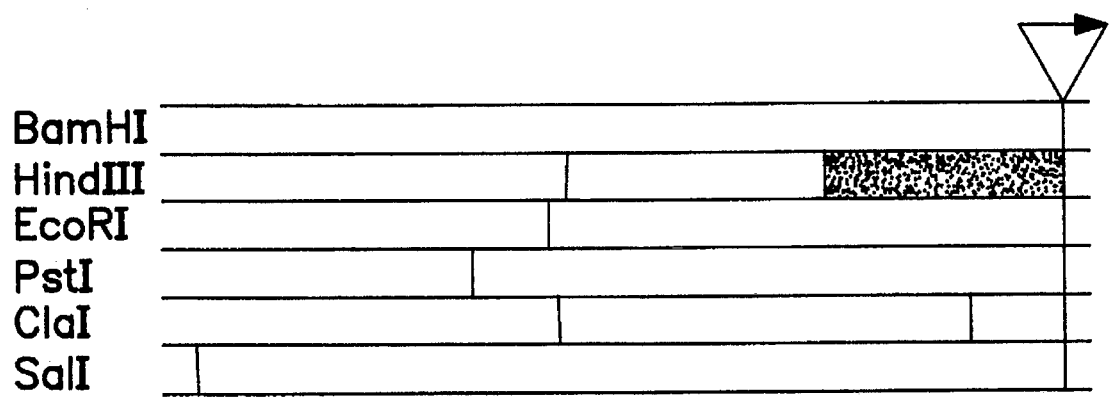
FIG. 4 Restriction map of the clone 12C4.

The strain SD6 was transformed by electroporation in accordance with the method of Becker and Guarente (in Methods in Enzymology vol 194 (1991) 182) (Jouan apparatus; 2500 V/cm; 80–100 ng of DNA/transformation) with the DNA of 11 pools of transduced elements obtained in A.4.2. (corresponding to a bank of 11,000 clones in *E. coli*). After 5 hours of regeneration in YPD medium (yeast extract 10 g/l; peptone 10 g/l; glucose 20 g/l), the cells were spread over minimum lactose medium. The transformants capable of growth on lactose were restreaked and, for each clone, the plasmid was extracted, amplified *in E. coli* and, after quick verification of the restriction map of the vector and of the mini-mu, used for retransformation of the yeast SD6. Among the clones of *K. lactis* obtained after retransformation, one of them, clone 12C4, was studied by restriction (cf. FIG. 4) and by analysis of the sequence of the junction between the *K. lactis* protein and the β-galactosidase. For this, the sequence of the junction, starting from the lacZ end of the mini-mu (double-stranded sequence), was determined by sequencing by means of the following oligonucleotide situated at −59 nucleotides from the junction:

5'-CTGTTTCATTTGAAGCGCG-3'    (SEQ ID No. 3)

Figure 5:
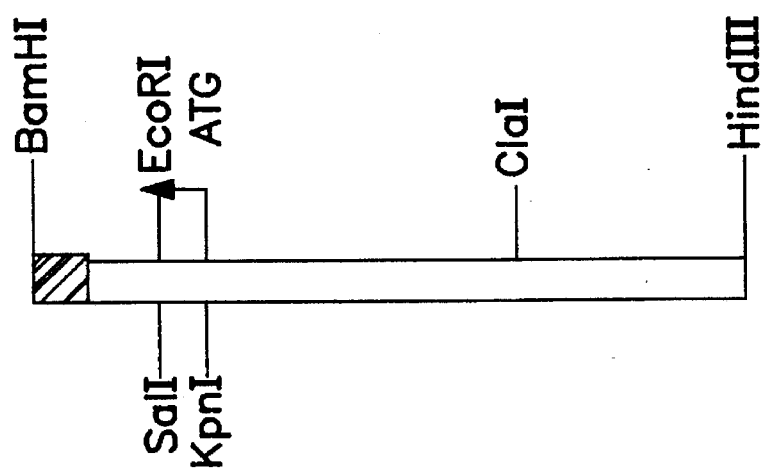
FIG. 5 Restriction map of the fragment BamHI-HindIII of 2.5 kb carrying the promoter KITAL1.

Analysis of the protein sequence deduced from the nucleotide sequence thus obtained by comparison with the sequences of the protein banks of other yeasts or eukaryotes (Genbank, MIPS, EMBL and the like) shows that the sequence carried by the clone 12C4 corresponds to the promoter of the gene of the transaldolase TAL1 of *K. lactis*. The BamHI-HindIII fragment of 2.5 kb containing the region upstream of the fusion was then sub-cloned in the vector Bluescript KS+ (stratagene), a restriction map was made (FIG. 5) and the sequence was determined by sequential deletions over about 1.3 kb (SEQ ID No. 1). Obtaining sequence elements also allows the expert to prepare specific probes and to reclone the promoter region according to the invention by hybridization in accordance with the conventional techniques of molecular biology.

II. Transformation of Kluyveronyces.

Various techniques enabling DNA to be introduced into the yeast can be used.

Advantageously, the various strains of Kluyveromyces used were transformed by treating the whole cells in the presence of lithium acetate and polyethylene glycol in accordance with the technique described by Ito et al. (J. Bacteriol. 153 (1983) 163–168). The transformation technique described by Durrens et al. (Curr. Genet. 18 (1990) 7), using ethylene glycol and dimethyl sulphoxide, was also used. It is also possible to transform the yeasts by electroporation, for example in accordance with the method described by Karube et al. (FEBS Letters 182 (1985) 90).

An alternative protocol has also been described in detail in the application EP 361 991.

III. Use of the Promoter of FIG. 1 for Expression of Heterologous Genes.

The transcriptional promoter activity of the region of *K. lactis* described on SEQ ID No. 1 was demonstrated at the time of its isolation, by its capacity to induce complementation of the lac4–8 mutation of the strain SD6. This capacity in fact results in expression of the gene lacZ of *E. coli*, and demonstrates by this the capacity for expression of heterologous genes.

IV. Construction of a Portable KlTAL1 Promoter

A portable promoter was prepared by PCR by inserting on the BamHI-HindIII fragment of 2.5 kb an HindIII restriction site in position +1 with respect to the ATG codon of the gene KlTAL1 and MluI and SalI restriction sites at 1197 pb upstream (SEQ ID No. 4). The PCR product is cloned in the vector pCRII (Kit TA Cloning™ System, Invitrogen), thus obtaining the vector pYG176. This construction enables the promoter KlTAL1 to emerge by MluI-HindIII digestion and facilitates cloning in the corresponding sites of the expression vector pYG1018 which contains the human preproalbumin gene under control of the promoter LAC4. The plasmid pYG1018 is identical to the vector pYG1023 described in the Patent EPA 402 212, except that it does not contain the BssHII-MluI fragment carrying the gene KlPGK.

5 μg of the vectors pYG176 and pYG1018 are digested by 60 units of HindIII and MluI. After migration on 0.8% agarose gel, the band of about 1.2 kb for pGY176 (corresponding to the promoter KlTAL1) and the bands of about 9 kb (corresponding to the vector part) and 2 kb (corresponding to the albumin fragment) for pYG1018 are electroeluted. Ligation at three partners (in accordance with the buffer and temperature recommendations defined by the supplier, New England Biolabs) is then carried out. The preparation of plasmids of transformants obtained after transformation of E. coli in accordance with the technique described by Chung and Miller [Nucleic Acids Res., 16 (1988) 3580] follows the method of alkaline lysis using SDS of Birnboim and Doly [Nucleic Acids Res., 6 (1979) 1513] modified by Ish-Horowicz and Burke [Nucleic Acids Res., 9 (1981) 2989]. After enzymatic digestion, the plasmid possessing the good restriction profile is designated pYG182 (FIG. 1).

Transformation of the strain CBS293.91 of K. lactis in accordance with the protocol described by Durrens et al. [Curr. Genetics, 18 (1990) 7] by 10 μg of pYG182 is effected. The transformants are selected on YPD medium (2% of glucose, 1% of yeast extract, 2% of bacto-peptone, 1.5% of bacto-agar), supplemented with the antibiotic geneticin (200 μg/ml).

The production of albumin by several transformants of the strain containing pYG182 is tested in accordance with the method described in the patent applications EP-A 361 991 and EP-A 521 767. The amount of albumin secreted by the various transformants is similar and can be estimated at about 50 mg/litre.

SUBSTITUTE

We claim:
1. A DNA sequence selected from the group consisting of:
   (a) SEQ ID No. 1 or its complementary strand;
   (b) SEQ ID No. 4 or its complementary strand; and
   (c) a fragment of (a) or (b); wherein said DNA sequence possesses transcriptional promoter activity.
2. A recombinant DNA comprising a DNA sequence according to claim 1.
3. A vector comprising the recombinant DNA of claim 2.
4. A recombinant DNA according to claim 2, further comprising one or more structural genes.
5. A recombinant DNA according to claim 4, further comprising signals which allow secretion of the expression products of said one or more structural genes.
6. A recombinant DNA according to claim 4, wherein the one or more structural genes code for proteins of pharmaceutical or agro-nutritional interest.
7. A recombinant DNA according to claim 6, wherein the one or more structural genes code for proteins selected from the group consisting of enzymes, blood proteins, insulin, lymphokines, growth factors, apolipoproteins, antigenic polypeptides for realization of vaccines, and fusion proteins.
8. The recombinant DNA according to claim 7, wherein said enzymes are selected from the group consisting of superoxide dismutase, catalase, amylases, lipases, amidases, and chymosin.
9. The recombinant DNA according to claim 7, wherein said blood derivatives are selected from the group consisting of serum albumin, alpha-globin, beta-globin, factor VIII, factor IX, von Willebrand factor (vWF), fibronectin and alpha$_1$-antitrypsin.
10. The recombinant DNA according to claim 7, wherein said lymphokines are selected from the group consisting of interleukins, interferons, colony stimulating factors, tumor necrosis factor (TNF), and T-cell replacing factor (TRF).
11. The recombinant DNA according to claim 10, wherein said colony stimulating factors are selected from the group consisting of granulocyte colony stimulating factor (G-CSF), granulocyte-macrophage stimulating factor (GM-CSF), and macrophage colony stimulating factor (M-CSF).

12. The recombinant DNA according to claim 7, wherein said growth factors are selected from the group consisting of growth hormone, erythropoietin, fibroblast growth factor (FGF), epidermal growth factor (EGF), platelet derived growth factor (PDGF), and transforming growth factor (TGF).

13. The recombinant DNA according to claim 7, wherein said antigenic polypeptides are selected from the group consisting of antigens from hepatitis, cytomegalovirus, Epstein-Barr virus, and herpes virus.

14. A recombinant cell containing a DNA sequence according to claim 1.

15. A recombinant cell according to claim 14, wherein said cell is a yeast.

16. A recombinant cell according to claim 15, wherein said cell is a yeast of the genus Kluyveromyces.

17. A process for the production of recombinant proteins, comprising culturing a recombinant cell according to claim 14 and recovering the proteins produced.

18. A process according to claim 17, wherein said proteins are of pharmaceutical or agro-nutritional interest.

19. A process according to claim 17, wherein the protein is human serum albumin.

* * * * *